United States Patent [19]

O'Neill

[11] 3,962,430

[45] June 8, 1976

[54] STERILIZATION OF SOLID NON-ELECTROLYTE MEDICINAL AGENTS EMPLOYING SODIUM CHLORIDE

[75] Inventor: Joseph L. O'Neill, Lafayette Hill, Pa.

[73] Assignee: Merck & Co., Inc., Rahway, N.J.

[22] Filed: July 14, 1975

[21] Appl. No.: 596,398

Related U.S. Application Data

[63] Continuation-in-part of Ser. No. 495,453, Aug. 7, 1974, abandoned, which is a continuation-in-part of Ser. No. 381,845, July 23, 1973, abandoned, which is a continuation-in-part of Ser. No. 160,570, July 7, 1971, abandoned, which is a continuation-in-part of Ser. No. 826,719, May 21, 1969, abandoned, which is a continuation-in-part of Ser. No. 485,592, Sept. 17, 1965, abandoned.

[52] U.S. Cl. ............................. 424/185; 424/238; 424/251; 424/263; 424/270; 424/273; 424/274; 424/346

[51] Int. Cl.² ........................................ A61K 31/69
[58] Field of Search ........... 424/185, 238, 251, 263, 424/270, 273, 274, 346

[56] References Cited
FOREIGN PATENTS OR APPLICATIONS
856,211   11/1970   Canada ............................ 424/153

OTHER PUBLICATIONS
Chemical Abstracts, vol. 41 (1947), p. 1776d.
Merck Index, 7th Ed. (1960), pp. 251, 287, 79, 349, 354, 381, 852, 864, 848, 1018.

*Primary Examiner*—V. D. Turner
*Attorney, Agent, or Firm*—Frank M. Mahon; Harry E. Westlake, Jr.

[57]   ABSTRACT

Sterilization of solid non-electrolyte medicinal agents by heating in an aqueous suspension which contains excess sodium chloride.

6 Claims, No Drawings

3,962,430

STERILIZATION OF SOLID NON-ELECTROLYTE MEDICINAL AGENTS EMPLOYING SODIUM CHLORIDE

This application is a continuation-in-part of U.S. Ser. No. 495,453, filed Aug. 7, 1974 now abandoned, which, in turn is a continuation-in-part of U.S. Application Ser. No. 381,845, filed July 23, 1973, now abandoned which, in turn is a continuation-in-part of U.S. application Ser. No. 160,570, filed July 7, 1971, now abandoned which, in turn, is a continuation-in-part of U.S. Ser. No. 826,719, filed May 21, 1969, now abandoned, which, in turn, is a continuation-in-part of U.S. Ser. No. 485,592, filed Sept. 17, 1965, now abandoned.

This invention relates to the sterilization of solid non-electrolyte corticosteroids, steroids and non-steroid medicinals. More specifically, the invention relates to the sterilization of solid non-electrolyte corticosteroids, selected from the group consisting of cortisone, cortisone acetate, dexamethasone, dexamethasone acetate, dexamethasone tertiary butyl acetate, hydrocortisone acetate, prednisolone acetate, betamethasone acetate, triamcinolone acetonide and methyl prednisolone, steroids selected from the group consisting of androsterone, 17-methyltestosterone, testosterone, testosterone borate, dienstrol, diethylstilbesterol, estradiol, estradiol-17-acetate, estradiol benzoate and ethinyl estradiol-3-methyl ether and non-steroids selected from the group consisting of propylidone, primidone, diphenylhydantoin, indomethacin and thiabendazole medicinals in the form of aqueous mixtures prior to their incorporation into sterile aqueous suspensions suitable for parenteral, ophthalmic or topical use.

Solid medicinals for use in aqueous suspensions are customarily sterilized in several ways, such as by aseptic crystallization, exposure to gases, for example, ethylene oxide; by use of chemical sterilizing agents added directly to the aqueous suspension, such as liquid propylene oxide, betapropiolactone, diethyl pyrocarbonate, etc.; and by dry heat sterilization. Certain disadvantages and hazards are characteristic of these known sterilizing processes. The known sterilization processes and techniques involved in aseptic crystallization and recrystallization of sterile solids within definite particle size ranges are expensive, subject to inadvertent microbial contamination with rejection of an entire production batch of crystallized solid for non-sterility and involves aseptic intrusions for sampling, sub-division, packaging and storage under sterile conditions. Most sterilizing agents effect sterility by alkylation. It is known that alkylating agents are also carcinogens. Furthermore, certain sterilizing agents which inactivate biologically active entitles by an alkylating degradation mechanism produce toxic end products or contaminants such as residual sterilizing agents and/or ethylene glycol. Moreover, sterilizing agents such as betapropiolactone hydrolyze into acidic end products which effect lower pH's. Trace amounts of moisture have been known to inactivate both betapropiolactone and diethyl pryocarbonate with no apparent physical change noted of these sterilizing agents. Also dry heat sterilization causes certain solid medicinal agents to undergo adverse physical and chemical changes such as discoloration and degradation of the solids even at temperatures below 120°C. For example, the corticosteroid, dexamethasone acetate, turns a brownish-yellow when subjected to dry heat at 100°C.

It is therefore an object of this invention to eliminate the prior complex and expensive processes and techniques involved in aseptic crystallization and recrystallization of sterile solids within predetermined particle size ranges.

It is another object of this invention to eliminate the problem of changes in particle size during the sterilization of solids having a predetermined particle size range for use in the preparation of a sterile suspension of such solids.

The above objects have been achieved in accordance with the process of this invention by the discovery that solid non-electrolyte medicinals of appropriate particle sizes or of a suitable particle size distribution may be sterilized by autoclaving (steam under pressure) the suspended drug in an aqueous mixture of sodium chloride, the concentration of which must be in excess of that required for a saturated sodium chloride solution at 100°C before application of heat to effect sterilization of the suspension system. Also, sterilization can be achieved by other means such as, for example, Tyndallization, in aqueous mixtures of excess sodium chloride. Preferably, a 10% excess of sodium chloride above the concentration necessary to form a saturated solution at 100% C. is incorporated to maintain an excess of NaCl above that of a saturated solution at elevated sterilization temperatures. The concentration of sodium chloride in this aqueous mixture with respect to the concentration of the medicinal agent employed may be such that the formulations after dilution with sterile water or sterile vehicle for final formula volume have a sodium chloride concentration which falls within the isotonic range. That is, the dilution to obtain each individual dosage concentration of the medicinal agent advantageously also dilutes the sodium chloride to an isotonic concentration.

The solid or solids for suspension may be prereduced to appropriate particle size by chemical or physical methods, such as crystallization, milling by ball or other mechanical means, or by the air attrition methods of jetomizing or microatomizing. For best results, all of the solid or solids should be below 10 microns, but it may be as large as 20 microns. In any event, 90% of it should be below 20, but preferably 10 microns.

Although the solubility in water of certain solid medicinals, which may be non-electrolyte salts or salt formers, intended for aqueous suspension may be described as being practically insoluble in water, the rate of solution and solubility of the majority of these solids increase in proportion to the elevation in temperature, such as that incidental to sterilization processes, i.e., from room temperature (20°–30°C.) to elevated temperatures, including autoclaving temperatures (110°–130°C.). Upon re-cooling the system to 20°–30°c., those solids that dissolve and redissolve at elevated temperatures are frequently recrystallized as different crystal forms with incident growth into different sizes and forms not acceptable for suspension purposes, for one reason or another.

Generally, the theory of the process of this invention is that since the solubility of non-electrolytes such as these solid medicinals intended for suspension in water are decreased by the addition of the electrolyte sodium chloride, and since sodium chloride ionizes upon solution and these ions require water for their hydration; therefore, in a saturated solution of sodium chloride there is little or no water available for solution of the non-electrolyte solid. Ideally, the solubility of sodium chloride in water is affected by less than 10% by variation in temperature from 25°C. to boiling point. Also, ideally sodium chloride is a neutral salt since it is a salt of a strong acid and base; therefore, solutions of sodium chloride do not effect the pH of aqueous systems. The addition of sodium chloride in a concentration sufficient to form saturated solutions at both room and elevated temperatures, plus a 10% excess, prevents the solution of the drugs at elevated temperatures, thus eliminating changes in crystal size and form upon recrystallization during subsequent cooling.

The essential ingredients necessary to maintain the original physical parameters during sterilization of the solid non-electrolyte medicinal agents employed herein are water and sodium chloride.

The amount of solid non-electrolyte medicinal agents employed in the practice of this invention is not critical. Preferably, the medicinal agents can be employed at ranges between 0.5 mg. to 100 mg. per ml. of water. Of particular preference is from 2 mg. to 50 mg. of medicinal agent per ml. of water.

The amount of sodium chloride employed in the practice of this invention can range between 1.1 mg. to 1.5 mg. per 2.6 mg. of water at 100°C. of particular preference is from 1.15 mg. to 1.25 mg. of sodium chloride per 2.6 mg. of water at 100°C.

While this invention has been found to be particularly useful in the preparation of aqueous suspensions of insoluble steroids, suitable for parenteral, topical and ophthalmic use, non-steroidal substances have also been sterilized by use of this process.

To show the value of the present invention over the prior art, an attempt was made to formulate an aqueous suspension of dexamethasone acetate for parenteral use by the heretofore utilized methods:

1. Aseptic recrystallization resulted in the formation of needle shaped crystals which could not be formulated into suitable aqueous suspensions for parenteral use;

2. Dry heat sterilization at temperature between 100°–120°C. resulted in discoloration of the dexamethasone acetate;

3. Sterilization by exposure to ethylene oxide gas was avoided because of degradation of the steroid by the alkylating agent;

4. Lyophilization of a sterile solution of dexamethasone acetate from dioxane and aseptic glass bead milling for particle size reduction resulted in an adverse change in crystal form;

5. Dexamethasone acetate jetomized to a particle size distribution of 90% below 10 microns and suspended in water or NaCl solutions having a concentration below that of saturated solutions at the sterilizing temperatures, then sterilized by autoclaving resulted in the growth of crystal sizes to 300 to 400 microns. Addition of salts to aqueous suspensions of dexamethasone acetate such as sodium citrate, sodium acid phosphate, or addition of concentrations of sodium chloride below the saturation level resulted in crystal size growth upon application of heat.

As one skilled in the art would appreciate, the amount of active ingredients which can be employed in the invention will depend on the specific therapeutic agent employed and the desired dosage of said therapeutic agent.

The following examples are included for the purpose of illustrating the process of this invention and are not to be construed as a limitation of the scope of this invention as hereinafter claimed.

EXAMPLE 1

A sterile aqueous suspension suitable for parenteral administration and having the following composition is as follows:

| | |
|---|---|
| Dexamethasone acetate | 8 mg. as alcohol |
| Sodium chloride | 8 mg. |
| Wetting agent | 0.75 mg. |
| Benzyl alcohol | 9 mg. |
| Sodium carboxymethyl-cellulose (LV) | 5 mg. |
| Water for injection q.s. ad. | 1 ml. |

Step A 8 mg. of sodium chloride is added to 16 mg. of water for injection hereinafter designated as water.

In those examples where a wetting agent is employed, said wetting agent is polyoxyethylene (20) sorbitan mono-oleate, a complex mixture of polyoxyethylene ethers of mixed partial oleic esters of sorbitol anhydrided. d. 1.06–1.10, viscosity 270–430 centistokes.

Complete solution of the sodium chloride must and does not occur even with the application of heat to the boiling point. The mixture is cooled to 80°–90°C. or any lower temperature down to room temperature. The dexamethasone acetate in a micro-fine form so that 90% of it is below 10 microns in size is added. The ease of wetting the micro-fine solid may be increased by the addition of an increment such as 10% of the formulated quantity of the wetting agent. The suspension in a sealed container is sterilized by autoclaving at 121°C. for 20–30 minutes time at temperature, then allowed to cool to room temperature.

Step B

The balance of the wetting agent and sodium carboxymethylcellulose are dissolved in 700 mg. of water. The benzyl alcohol is added and dissolved. This solution is clarified by filtration such as through a sintered glass filter, and then sterilized by autoclaving at 121°C. time at temperature, for a minimum of 15 minutes.

Step C

The resultant product of Step A is combined with the resultant product of Step B aseptically and sterile water is added aseptically to 100 parts or 1 ml. The suspension system is homogenized aseptically and divided under aseptic, sterile conditions into sterile ampules or multi-dose vials. The sodium chloride concentration of this dosage form preparation is isotonic.

The dexamethasone acetate contained in the sterile suspension prepared in accordance with this method showed no crystal size growth. X-ray analysis indicated no change in crystal form. Analytical studies, including infra-red analysis, indicated intact dexamethasone acetate with no decomposition even after autoclaving the steroid-sodium chloride mixture in Step A for 1 hour at 121°C.

EXAMPLE 2

A sterile aqueous suspension suitable for parenteral administration and having a composition similar to that produced by Example 1 can be prepared by replacing the sodium carboxymethylcellulose (LV) with 50% aqueous sorbitol.

EXAMPLE 3

A sterile aqueous suspension suitable for parenteral administration and having a composition similar to those of Examples 1 and 2, but containing 2 mg. dexamethasone alcohol per ml. represented as dexamethasone acetate, may be prepared by reducing the concentration of wetting agent to 0.037% by weight.

EXAMPLE 4

A sterile aqueous suspension suitable for parenteral administration, and having a similar composition as Examples 1 and 2 but containing 18 mg. dexamethasone alcohol per ml. incorporated as dexamethasone acetate, may be prepared, in which case the concentration of wetting agent is increased to 0.2%.

EXAMPLE 5

A sterile aqueous suspension suitable for parenteral use and having the following composition and prepared in a manner similar to Example 1 is as follows:

| | |
|---|---|
| Dexamethasone acetate | 8 mg. as alcohol |
| Dexamethasone phosphate | 2 mg. as alcohol |
| Benzyl alcohol | 9 mg. |
| Sodium chloride | 6.67 mg. |
| Sodium carboxymethyl-cellulose (LV) | 5 mg. |
| Creatinine | 5 mg. |
| Wetting agent | 0.75 mg. |
| Sodium bisulfite | 1.0 mg. |
| EDTA disodium | 0.5 mg. |
| Sodium hydroxide q.s. pH | 6.8 |
| Water for injection q.s ad. | 1 ml. |

Step A

The 6.67 mg. by weight of sodium chloride is added to 15 mg. water, then the procedure of Example 1, Part A, is followed.

Step B

The sodium carboxymethylcellulose (LV) is dissolved in 400 mg. of the water, clarified by filtration, sterilized by autoclaving at least 15 minutes time at a temperature of 121°C.

Step C

The balance of the ingredients are dissolved in 40 mg. of water and this solution is sterilized by filtration through a sterilizing filter.

Step D

The product of Step A is combined with the product of Step B, and this then with the product of Step C. Then sterile water is added to make 100 parts (1.0 ml). The suspension is circulated through a homogenizer at 1500–300 p.s.i., then collected in a sterile receiving vessel suitable for aseptic sub-division of a suspension. The suspension is then sub-divided aseptically.

The chemical stability and physical stability of this suspension has been observed over a period of three years. Chemical assays were above 100% of that of the label claim after 1 year. The particle size was measured microscopically using a graduated micron scale, and particle size distribution curves were obtained using a Coulter counter. Microscopically, little to no growth was observed of crystal size after three years at room temperature. However, some crystal growth was noted in the 37°C. and 50°C. storage temperature samples even after three to six months storage. Crystal growth at the elevated temperatures result in increased solution of dexamethasone acetate recrystallized into larger crystal sizes to a maximum of 50–60 microns at 50°C. Particle size distribution curves after 1 year at room temperature measured by the Coulter counter yielded results of 90% below 18 microns and 0% above 28 microns. The particles in this suspension are flocculated and the Coulter counter does not differentiate between single particles and flocs. The initial Coulter counter curve has shown 90% below 17 microns, none above 25 microns.

EXAMPLE 6

A sterile aqueous suspension suitable for parenteral administration and having a similar composition as that of the product of Example 5 may be prepared by increasing the dexamethasone alcohol content to 18 mg. alcohol per ml. added as dexamethasone acetate. In this case the concentration of wetting agent is increased to 2 mg. per ml. This suspension has been prepared using both autoclaved and non-autoclaved dexamethasone acetate. The autoclaved dexamethasone acetate in suspension contains 90% of its particles below 13.5 microns whereas the non-autoclaved steroid in suspension measured 90% below 11.5 microns. Neither of the two suspensions had particles above 30 microns. The jetomized steroid prior to formulation of both the autoclaved and the non-autoclaved compounds contained particles 90% below 8.5 microns for the latter. A similar small increase in particle size resulted in both suspensions containing either autoclaved or non-autoclaved steroids immediately under formulation as measured by the Coulter counter and indicates the measurement of not only individual crystals but flocs of crystals of the lower particle sizes. It must be noted that the suspension containing the non-autoclaved dexamethasone acetate was not sterile.

EXAMPLE 7

A sterile aqueous suspension suitable for parenteral use and having a similar composition as that of Example 5 but containing 2 mg. alcohol per ml. added as dexamethasone acetate may be prepared, in which case the concentration of wetting agent is reduced to 0.375 mg. per ml.

EXAMPLE 8

A sterile aqueous suspension suitable for parenteral use and having a similar composition as that of Example 5, but containing no dexamethasone phosphate.

EXAMPLE 9

A sterile aqueous suspension suitable for parenteral use and having a similar composition to that of the product of Examples 5, 6 and 7, but containing 50% sorbitol in place of the sodium carboxymethylcellulose (LV) may be prepared.

EXAMPLE 10

A sterile aqueous suspension suitable for parenteral use containing lidocaine hydrochloride may be prepared having the followimg composition:

| | |
|---|---|
| Dexamethasone acetate | 8 mg. alcohol |
| Dexamethasone phosphate | 2 mg. alcohol |

-continued

| | |
|---|---|
| Lidocaine hydrochloride | 10 mg. |
| Sodium bisulfite | 1 mg. |
| EDTA disodium | 0.5 mg. |
| Creatinine | 5.0 mg. |
| Wetting agent | 2.0 mg. |
| Sodium carboxymethylcellulose (LV) | 5.0 mg. |
| Benzyl alcohol | 9.0 mg. |
| Sodium chloride | 6.67 mg. |
| Sodium hydroxide   q.s.   pH | 6.8 |
| Water for injection q.s.   ad | 1 ml. |

This composition may be prepared in accordance with the procedure set forth in Examples 5, 6 and 7; however, the lidocaine hydrochloride can be added as either the base converted to the hydrochloride prior to the addition using hydrochloric acid or as the hydrochloride salt. The pH of the suspension is adjusted to 6.8 to maintain solution of the lidocaine, and for optimum steroid phosphate stability. The solution of the lidocaine hydrochloride is added (see Example 4) to the product of Step C prior to sterilization by filtration.

EXAMPLE 11

A sterile aqueous suspension suitable for ophthalmic use and having the following composition is as follows:

| | mg. per ml. |
|---|---|
| Hydrocortisone alcohol microcrystalline 90% below 10 microns | 10.0 mg. |
| Sodium chloride | 8.0 mg. |
| Phenethyl alcohol | 5.0 mg. |
| Wetting agent | 2.0 mg. |
| EDTA disodium | 0.5 mg. |
| Sodium carboxymethylcellulose (LV) | 5.0 mg. |
| Water for injection q.s.   ad. | 1.0 ml. |

Step A 8 mg. of sodium chloride is added to 18 mg. of water for injection. Then the procedure is identical to Example 1, Part A, except that the hydrocortisone compound is added in place of the dexamethasone.

Step B

Identical to Example 1, Step B.

Step C

Identical to Example 1, Step C.

Step D

Identical to Example 1, Step D, except that the product is sub-divided into sterile glass or plastic containers suitable for ophthalmic use. This product has shown excellent physical and chemical stability data over a period of 6 months.

EXAMPLE 12

A sterile aqueous suspension suitable for parenteral use containing prednisolone tertiary butyl acetate is as follows:

| | mg. per ml. |
|---|---|
| Prednisolone tertiary butyl acetate (microcrystalline) 90% below 10 microns | 20 mg. |
| Benzyl alcohol | 9 mg. |
| Sodium chloride | 8 mg. |
| Sodium carboxymethylcellulose (LV) | 5 mg. |
| Wetting agent | 2 mg. |
| Water for injection q.s.   ad. | 1 mg. |

Prepared in the same manner as Example 1.

EXAMPLE 13

Other examples using other steroids, betamethasone acetate, triamcinolone acetonide, and methyl prednisolone acetate have been sterilized using this invention. When using conventional methods of steam sterilization or tyndallization, betamethasone acetate was observed and crystal size showed growth from maximums of 70 micron needles to 400–500 micron long needles, which are not suitable for parenteral use. The above examples disclose several corticosteroids but the invention includes substituting for them other corticosteroids such as cortisone, cortisone acetate, dexamethasone, dexamethasone tertiary butyl acetate, hydrocortisone acetate, prednisolone and prednisolone acetate.

Instead of the corticosteroids, the invention includes the substitution in the above examples of the several pharmaceutical androgens. Representative ones are androsterone, 17 methyltestosterone, testosterone and testosterone borate.

Instead of the corticosteroids, the invention includes the substitution in the above examples of the several pharmaceutical estrogens. Representative ones are dienstrol, diethylstibesterol, estradiol, estradiol 17 acetate, estradiol benzoate and ethinyl estradiol 3 methyl ether.

Non-steroid substances have also been sterilized using this invention for both ophthalmic and parenteral use and are illustrated in Examples 14 to 18. In these examples, instead of the therapeutic agents mentioned, the invention contemplates the substitution of propylidone (radio opaque), primidone (anti-convulsant), and diphenylhydantoin (anti-convulsant).

EXAMPLE 14

A sterile aqueous suspension of a non-steroidal anti-inflammatory agent (indomethacin) suitable for parenteral administration, particularly for IM and IA injection, and having the following composition, has been prepared:

| | mg. per ml. |
|---|---|
| Indomethacin | 50 mg. |
| Lecithin | 1 mg. |
| Benzyl alcohol | 9 mg. |
| Wetting agent | 2 mg. |
| Sodium chloride | 8 mg. |
| EDTA disodium | 0.5 mg. |
| Sodium bisulfite | 1 mg. |
| Sodium carboxymethylcellulose (LV) | 5 mg. |
| Sodium hydroxide   q.s.   pH | 5–6 |
| Water for injection   q.s.   ad. | 1 ml. |

Step A

The indomethacin is sterilized in a manner identical to that of Example 1, Step A, except that one-half of the formulated amount of sodium bisulfite is included here.

Step B

The lecithin is dissolved in 100 mg. of water, clarified by filtration through a coarse sintered glass filter, and sterilized by autoclaving at 121°C. for 15 minutes.

Step C

The sodium carboxymethylcellulose (LV) is prepared in the manner identical to that of Example 4, Step B, except that only 300 mg. of water are used.

Step D

The balance of ingredients are prepared in the same manner as in Example 5, Step C.

Step E

Upon cooling to room temperature, the product of Step B is added to the product of Step A and the mixture agitated for 15 minutes, and then added to the combination of the product of Step C and Step D, whereupon the formula is brought to volume with water and agitated for one-half hour. The resulting suspension is homogenized as in the previous examples and sub-divided into containers suitable for parenteral use.

EXAMPLE 15

The products of Examples 12 and 14 can be prepared by using 50% aqueous sorbitol in place of the sodium carboxymethylcellulose.

EXAMPLE 16

An ophthalmic suspension of indomethacin and prepared in accordance with Example 14 is as follows:

|  | mg. per ml. |
|---|---|
| Indomethacin jetomized | 10.0 mg. |
| Lecithin | 0.2 mg. |
| EDTA disodium | 0.5 mg. |
| Sodium chloride | 6.67 mg. |
| Sodium bisulfite | 1.0 mg. |
| Sodium citrate | 1.8 mg. |
| Citric acid | 0.2 mg. |
| Phenethyl alcohol | 5.0 mg. |
| Wetting agent | 2.0 mg. |
| Sorbitol solution 70% | 10.0 mg. |
| Water for injection q.s. ad. | 1 ml. |

EXAMPLE 17

The products of Examples 14 and 16 can be prepared with concentrations of indomethacin, 5–50 mg. per ml., but the concentration of lecithin in these cases must be kept proportional to the concentration of indomethacin, i.e., 0.4 mg. lecithin to each 20 mg. indomethacin.

EXAMPLE 18

An ophthalmic or topical suspension of thiabendazole, an anti-fungal agent, may be prepared in a manner identical to that of Example 5, and has the following composition:

|  | mg. per ml. |
|---|---|
| Thiabendazole jetomized | 40 mg. |
| Phenethyl alcohol | 5 mg. |
| Benzalkonium chloride | 0.2 mg. |
| Sorbitol solution 70% | 10 mg. |
| Hydroxyethylcellulose | 1 mg. |
| EDTA disodium | 0.5 mg. |
| Sodium chloride | 8.0 mg. |
| Water for injection q.s. ad. | 1 ml. |

In this composition, the hydroxyethylcellulose replaced the sodium carboxymethylcellulose of the former example.

EXAMPLE 19

A sterile aqueous suspension suitable for parenteral administration and having the following composition is as follows:

| Dexamethasone acetate | 8 mg. as alcohol |
|---|---|
| Sodium chloride | 9 mg. |
| Water for injection q.s. ad. | 1 ml. |

9 mg. of sodium chloride is added to 16 mg. of water. Complete solution of the sodium chloride must and does not occur even with the application of heat to the boiling point. The mixture is cooled to 80°–90°C. or any lower temperature down to room temperature. The dexamethasone acetate in a micro-fine form so that 90% of it is below 10 microns in size is added. The suspension in a sealed container is sterilized by autoclaving at 121°C. for 20–30 minutes time at temperature, then allowed to cool to room temperature and sterile water is added aseptically to 100 parts or 1 ml. The suspension system is homogenized aseptically and divided under aseptic, sterile conditions into sterile ampules or single dose vials. The sodium chloride concentration of this dosage form preparation is isotonic.

EXAMPLE 20

A sterile aqueous suspension suitable for parenteral administration can be prepared having a composition similar to that of Example 9, but containing 2 mg. dexamethasone alcohol per ml. represented as dexamethasone acetate.

EXAMPLE 21

A sterile aqueous suspension suitable for parenteral administration can be prepared having a similar composition as Example 19 but containing 18 mg. dexamethasone alcohol per ml. incorporated as dexamethasone acetate.

EXAMPLE 22

A sterile aqueous suspension suitable for parenteral use and having the following composition and prepared in a manner similar to Example 19 is as follows:

| Dexamethasone acetate | 8 mg. as alcohol |
|---|---|
| Dexamethasone phosphate | 2 mg. as alcohol |
| Sodium chloride | 8.0 mg. |
| Water for injection q.s. ad. | 1 ml. |

Step A

The 8.0 mg. by weight of sodium chloride are added to 16 mg. water, then the procedure of Example 19 is followed.

Step B

Dexamethasone phosphate is dissolved in 40 mg. of water and this solution is sterilized by filtration through a sterilizing filter.

Step C

The product of Step A is combined with the product of Step B, then sterile water is added to make 100 parts (1.0 ml). The suspension is circulated through a homogenizer at 1500–3000 p.s.i., then collected in a sterile receiving vessel suitable for aseptic sub-division of a suspension. The suspension is then sub-divided aseptically.

EXAMPLE 23

A sterile aqueous suspension suitable for parenteral administration and having a similar composition as that of the product of Example 22 may be prepared by increasing the dexamethasone alcohol content to 18 mg. alcohol per ml. added as dexamethasone acetate.

EXAMPLE 24

A sterile aqueous suspension suitable for parenteral use and having a similar composition as that of Example 22 but containing 2 mg. alcohol per ml. added as dexamethasone acetate may be prepared.

EXAMPLE 25

A sterile aqueous suspension of a non-steroidal anti-inflammatory agent (indomethacin) suitable for parenteral administration, particularly for parenteral and opthalmic applications and having the following composition, has been prepared:

|  | mg. per ml. |
|---|---|
| Indomethacin | 50 mg. |
| Sodium chloride | 8 mg. |
| Sodium bisulfite | 1 mg. |
| Water for injection q.s. ad. | 1 ml. |

The indomethacin is sterilized in a manner identical to that of Example 19, except the sodium bisulfite is included herein. Upon cooling to room temperature, the formula is brought to volume with water and agitated for one-half hour. The resulting suspension is homogenized as in the previous examples and subdivided into containers suitable for parenteral use.

EXAMPLE 26

The product of Example 25 can be prepared with concentrations of indomethacin ranging from about 5–50 mg. per ml.

EXAMPLE 27

An ophthalmic or topical suspension of thiabendazole, an anti-fungal agent, may be prepared in a manner identical to that of Example 19, and has the following composition:

|  | mg. per ml. |
|---|---|
| Thiabendazole jetomized | 40 mg. |
| Sodium chloride | 9.0 mg. |
| Water for injection q.s. ad. | 1 ml. |

EXAMPLE 28

A sterile aqueous suspension suitable for parenteral administration and having the following composition is as follows:

| Testosterone | 100 mg. |
|---|---|
| Sodium Chloride | 9 mg. |
| Water for injection q.s. ad. | 1 ml. |

9 mg. of sodium chloride is added to 16 mg. of water. Complete solution of the sodium chloride must and does not occur even with the application of heat to the boiling point. The mixture is cooled to 80°–90°C. or any lower temperature down to room temperature. The dexamethasone acetate in a micro-fine form so that 90% of it is below 10 microns in size is added. The suspension in a sealed container is sterilized by autoclaving at 121°C. for 20–30 minutes time at temperature, then allowed to cool to room temperature and sterile water is added aseptically to 100 parts or 1 ml. The suspension system is homogenized aseptically and divided under aseptic, sterile conditions into sterile ampules or single dose vials. The sodium chloride concentration of this dosage form preparation is isotonic.

EXAMPLE 29

A sterile aqueous suspension suitable for parenteral administration and having a similar composition as that of Example 27 can be prepared by substituting androsterone, 17-methyltestosterone or testosterone borate for testesterone.

EXAMPLE 30

A sterile aqueous suspension suitable for parenteral administration and having the following composition is as follows:

| Estradiol | 50 mg. |
|---|---|
| Sodium chloride | 9 mg. |
| Water for injection q.s. ad. | 1 ml. |

9 mg. of sodium chloride is added to 16 mg. of water. Complete solution of the sodium chloride must and does not occur even with the application of heat to the boiling point. The mixture is cooled to 80°–90°C. or any lower temperature down to room temperature. The dexamethasone acetate in a micro-fine form so that 90% of it is below 10 microns in size is added. The suspension in a sealed container is sterilized by autoclaving at 121°C. for 20–30 minutes time at temperature, then allowed to cool to room temperature and sterile water is added aseptically to 100 parts or 1 ml. The suspension system is homogenized aseptically and divided under aseptic, sterile conditions into sterile ampules or single dose vials. The sodium chloride concentration of this dosage form preparation is isotonic.

EXAMPLE 31

A sterile aqueous suspension suitable for parenteral administration and having a similar composition as that of Example 29 can be prepared by substituting dienstrol, diethylstiblesterol, estradiol-17-acetate or estradiol benzoate for estradiol.

There are many advantages incident to the use of the process of this invention. Complex and expensive processes involved in the provision of sterile solids having pre-determined particle size ranges are avoided, and aseptic intrusion for sampling, sub-division, packaging and storage of a sterilized solid under sterile conditions are eliminated. Discoloration of sterile solids by dry heat sterilization is also eliminated.

I claim:

1. A process for preparing a sterile isotonic aqueous pharmaceutical suspension of a solid non-electrolyte medicinal agent selected from the group consisting of a corticosteroid, a steroid and a non-steroid wherein the corticosteroid is selected from the group consisting of cortisone, cortisone acetate, dexamethasone, dexamethasone acetate, dexamethasone tertiary butyl acetate, hydrocortisone acetate, predisolone, prednisolone acetate, betamethasone acetate, triamcinolone acetonide and methyl prednisolone; the steroid is selected from the group consisting of androsterone, 17-methyltestosterone, testosterone, testosterone borate, dienstrol, diethylstilbesterol, estradiol, estradiol-17-acetate, estradiol benzoate and ethinyl estradiol-3-methyl ether; and the non-steroid is selected from the group consisting of propylidone, primidone, diphenylhydantoin, indomethacin and thiabendazole, which comprises adding the medicinal agent to a mixture of sodium chloride and water, the concentration of sodium chloride being sufficient for a saturated solution at 100°C, heating at a temperature of from about 100°–130°C for a time sufficient to sterilize the medicinal agent and the aqueous system and after cooling to room temperature, adding sterile water for dilution to obtain the desired concentration of said medicinal agent in an effective amount in suspension.

2. The process of claim 1 wherein sodium chloride is present up to 10% excess over saturation.

3. The process of claim 2 wherein the sodium chloride is present at about 10% excess.

4. The process of claim 1 wherein the medicinal agent is a steroid.

5. The process of claim 1 wherein the medicinal agent is a corticosteroid.

6. The process of claim 1 wherein the medicinal agent is a non-steroid.

* * * * *